United States Patent
Joo et al.

(10) Patent No.: US 9,896,657 B2
(45) Date of Patent: Feb. 20, 2018

(54) METHOD OF INDUCING DIFFERENTIATION OF STEM CELL INTO CORNEAL LIMBAL STEM CELL

(71) Applicant: THE CATHOLIC UNIVERSITY OF KOREA INDUSTRY-ACADEMIC COOPERATION FOUNDATION, Seoul (KR)

(72) Inventors: Choun-Ki Joo, Seoul (KR); Hyun Soo Lee, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 57 days.

(21) Appl. No.: 14/823,187

(22) Filed: Aug. 11, 2015

(65) Prior Publication Data

US 2016/0304836 A1 Oct. 20, 2016

(30) Foreign Application Priority Data

Apr. 14, 2015 (KR) ........................ 10-2015-0052198

(51) Int. Cl.
C12N 15/00 (2006.01)
C12N 5/0797 (2010.01)
A61K 35/30 (2015.01)

(52) U.S. Cl.
CPC ............ *C12N 5/0623* (2013.01); *A61K 35/30* (2013.01); *C12N 2500/46* (2013.01); *C12N 2500/84* (2013.01); *C12N 2501/11* (2013.01); *C12N 2501/155* (2013.01); *C12N 2501/33* (2013.01); *C12N 2501/39* (2013.01)

(58) Field of Classification Search
CPC .................................................. A61K 35/30
See application file for complete search history.

(56) References Cited

U.S. PATENT DOCUMENTS

2013/0251692 A1* 9/2013 Itskovitz-Eldor .... C12N 5/0621
424/93.7

FOREIGN PATENT DOCUMENTS

KR 2014-0125682 A 10/2014

OTHER PUBLICATIONS

Brevini et al., 2010, Theriogenology, vol. 74, pp. 544-550.*
Paris et al. (2010, Theriogenology, vol. 74, pp. 516-524).*
Munoz et al. (2008, Theriogenology, vol. 69, pp. 1159-1164).*
Gomez et al. (2010, Theriogenology, vol. 74, pp. 498-515).*
Jean et al. (2013, Develop. Growth Differ., vol. 55, pp. 41-51).*
Buta et al. (2013, Stem Cell Res., vol. 11, pp. 552-562).*
Ekici et al. (e-Pub Jan. 2015, Medicine Science, pp. 1-11).*
Shalom-Feurstein et al. (2012, Stem Cells, vol. 30, pp. 898-909).*
2004, Qi et al., PNAS, vol. 101(16), pp. 6027-6032.*
2016, Morikawa et al., Stem Cell Reports, vol. 6, pp. 64-73.*
Harminder et al. 2000, Survey of Ophthalmology, vol. 44(5), pp. 415-425.*
1st Korean Office Action for 10-2015-0052198, untranslated, dated Oct. 28, 2016, 5 pages.
Lee et al., "Differentiation of human induced pluripotent stem cells into corneal limbal progenitor cells", Investigative Ophthalmology & Visual Science dated Apr. 2014, vol. 55, 2 pages. Abstract Only.
Loureiro et al., "Comparison of culture media for ex vivo cultivation of limbal epithelial progenitor cells", Molecular Vision 2013; 19:67-77.
Kruse et al., "A serum-free clonal growth assay for limbal, peripheral, and central corneal epithelium", Invest Ophthalmol Vis Sci, Jun. 1991; 32(7):2086-95. Abstract Only.

* cited by examiner

*Primary Examiner* — Thaian N Ton
(74) *Attorney, Agent, or Firm* — Lathrop Gage LLP

(57) ABSTRACT

The present invention relates to a method of inducing differentiation of a stem cell into a corneal limbal stem cell, and a medium composition used therein. Further, the present invention relates to a pharmaceutical composition for treating corneal damage, including a corneal limbal stem cell differentiated using the above-described method as an active ingredient.

5 Claims, 2 Drawing Sheets

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: K3-F primer

<400> SEQUENCE: 1
ggcagagatc gagggtgtc

```
<210> SEQ ID NO 2
<211> LENGTH: 21
<212> TYPE: DNA
<213> ORGANISM: Artificial Sequence
<220> FEATURE:
<223> OTHER INFORMATION: K3-R primer

<400> SEQUENCE: 2
gtcatccttc gcctgctgta g                                      21

<210> SEQ ID NO 3
<211> LENGTH: 20
<212> TYPE: DNA
<213> ORGANISM: Artificial Sequence
<220> FEATURE:
<223> OTHER INFORMATION: ABCG2-F primer

<400> SEQUENCE: 3
accattgcat cttggctgtc                                        20

<210> SEQ ID NO 4
<211> LENGTH: 20
<212> TYPE: DNA
<213> ORGANISM: Artificial Sequence
<220> FEATURE:
<223> OTHER INFORMATION: ABCG2-R primer

<400> SEQUENCE: 4
cgatgccctg ctttaccaaa                                        20

<210> SEQ ID NO 5
<211> LENGTH: 20
<212> TYPE: DNA
<213> ORGANISM: Artificial Sequence
<220> FEATURE:
<223> OTHER INFORMATION: p63-F primer

<400> SEQUENCE: 5
caactgctca aaggcacaaa                                        20

<210> SEQ ID NO 6
<211> LENGTH: 20
<212> TYPE: DNA
<213> ORGANISM: Artificial Sequence
<220> FEATURE:
<223> OTHER INFORMATION: p63-R primer

<400> SEQUENCE: 6
cctcccagga aacaacagaa                                        20
```

METHOD OF INDUCING DIFFERENTIATION OF STEM CELL INTO CORNEAL LIMBAL STEM CELL

TECHNICAL FIELD

The present invention relates to a method of inducing differentiation of a stem cell into a corneal limbal stem cell, and a medium composition used therein. Further, the present invention relates to a pharmaceutical composition for treating corneal damage, including a corneal limbal stem cell differentiated using the above-described method as an active ingredient.

BACKGROUND ART

Stem cells refer to cells which are in a pre-differentiation stage prior to the stage of differentiating into cells forming respective tissues, and refer to cells which are in an undifferentiated state where they exhibit the ability of self-renewal by which the cells may proliferate infinitely and pluripotency which is potential by which the cells may differentiate into a diverse range of cell types of tissues by specific differentiation stimulation. That is, it is required for the stem cells that the ability of self-renewal of the cell is maintained without decreasing even when the cells are continuously cultured, and the cells may differentiate into various types of cells. The stem cells include embryonic stem cells, adult stem cells, induced pluripotent stem cells (iPS cells), etc.

Among them, the induced pluripotent stem cells denote cells restored to be in the pluripotent cell stage which is the early stage of cell production like embryonic stem cells by restoring completely differentiated somatic cells to be in an undifferentiated cell stage. When the induced pluripotent stem cells are induced to differentiate using somatic cells isolated from one's own body, there is no problem of transplant rejection, and since any egg or embryo is used for preparing the induced pluripotent stem cells, ethical issues are addressed. In this respect, many scientists have expected the induced pluripotent stem cells to fundamentally resolve the treatment of various diseases and organ damage.

In this point of view, a lot of methods of differentiation of the induced pluripotent stem cells into many cells and many techniques for treating diseases using the above-described methods have been developed, and Korean Unexamined Patent Application Publication No. 2014-0125682 disclosed "Pharmaceutical Composition for the Treatment of Stroke Comprising Neural Precursor Cells Derived from Human Induced Pluripotent Stem Cells".

However, the stem cells are undifferentiated cells, it is difficult to predict which type of cells into which the stem cells later differentiate, and there may be a problem of mutations or genetic abnormalities. Accordingly, when the stem cells are to be used, there is a need for techniques by which the stem cell may be induced to differentiate into a specific type of cell.

Meanwhile, a cornea is the transparent layer of the eye surface positioned at the center portion of the eye, which is an organ protecting the eye from the outside. The external side of the cornea is an epithelial layer, which is a protecting layer of a tissue which is regenerated despite being damaged. However, Bowman's membrane and corneal endothelial which are located at a more inner side than an epithelial layer are not regenerated once damaged.

Consequently, the inner side of the epithelial layer in the cornea of the eye is not regenerated once damaged, and thus vision may be severely impaired or lost. Accordingly, there is a need to perform a surgical treatment for the cornea or replace the cornea through corneal transplantation, etc.

However, regarding corneal transplantation, infants are difficult to remain stable after corneal transplantation, various complications may develop, there may be the problem of immunological rejection because a donor cornea is transplanted, and when patients with corneal dystrophy have corneal transplants, corneal dystrophy is likely to recur. Moreover, there is a severe lack of donated corneas to perform corneal transplant.

With such a background, the inventors of the present invention determined a method of inducing differentiation of a stem cell into a corneal limbal stem cell which is necessary for cornea regeneration, thereby completing the present invention.

SUMMARY OF THE INVENTION

The objective of the present invention is to provide a method of inducing differentiation of a stem cell into a corneal limbal stem cell, including culturing a stem cell in a medium including BMP-4 (bone morphogenetic protein-4).

Another objective of the present invention is to provide a pharmaceutical composition for treating corneal damage, including a corneal limbal stem cell differentiated from a stem cell using the method as an active ingredient according to the present invention.

Yet another objective of the present invention is to provide a medium composition for inducing differentiation of a stem cell into a corneal limbal stem cell, including BMP-4.

In order to achieve the above-described objectives, it was determined whether a corneal limbal stem cell was differentiated or not after culturing an induced pluripotent stem cell which is a type of stem cell in a differentiation-inducing medium including BMP-4.

As a result, it was determined that the cell had a round-spindle shape, the expression of K3 which is a marker of epithelial cells decreased, and the expression of ABCG2 and p63 which are markers of corneal limbal stem cells increased, and thus the stem cell was differentiated into the corneal limbal stem cell.

As described above, the present invention proved that a corneal limbal stem cell may be differentiated from a stem cell. The differentiated corneal limbal stem cell may be used to restore a damaged cornea.

Hereinafter, the present invention will be described in detail.

According to an embodiment according to the present invention, the present invention relates to a method of inducing differentiation of a stem cell into a corneal limbal stem cell, including culturing a stem cell in a medium including BMP-4.

According to another embodiment according to the present invention, the present invention relates to a medium composition for inducing differentiation of a stem cell into a corneal limbal stem cell, including BMP-4.

According to still another embodiment according to the present invention, the present invention relates to a medium composition for inducing differentiation of a stem cell into a corneal limbal stem cell, the medium composition prepared by adding BMP-4 to a medium in which a medium including epidermal growth factor (EGF), insulin, hydrocortisone, ethanolamine, phosphoethanolamine and bovine pituitary extract (BPF), and an Iscove's modified Dulbecco's medium (IMDM) supplemented with fetal bovine serum (FBS) are mixed in a ratio of 1:2 to 2:1.

In the present invention, the term "stem cell" refers to a cell having pluripotency by which the cell may differentiate into cells derived from the endoderm, mesoderm and ectoderm of animals, or limited multipotency by which the cell may differentiate into cells closely related to the organization or function of the cells. The stem cell according to the present invention is not limited, as a specific example, may be an induced pluripotent stem cell or an embryonic stem cell (ESC).

In the present invention, the term "induced pluripotent stem cell" refers to a cell having potential by which the cell may proliferate infinitely (self-renewal) while maintaining pluripotency like an embryonic stem cell by restoring a completely differentiated cell to be in an undifferentiated cell stage. In the present invention, induced pluripotent stem cells may be stem cells dedifferentiated from various cells, for example, may be dedifferentiated from fibroblasts, blood cells, and the like, but are not limited thereto.

Further, examples of methods of dedifferentiating induced pluripotent stem cells from various cells include a compound treatment method, a genetic transformation method, a method of culturing cells under specific conditions, or the like, but are not limited thereto. For example, dedifferentiation may be induced by introducing reprogramming-related genes such as Oct4, Sox2, Klf4, c-Myc, and the like for expression into a differentiated cell, but the method is not limited thereto.

Further, an embryonic stem cell is obtained by extracting the inner cell mass (ICM) from the embryo at the blastula stage before the fertilized egg is implanted in mother's womb and culturing the inner cell mass in vitro, and denotes a cell having plutipotency to differentiate into any animal cell.

In the present invention, the term "BMP-4 (bone morphogenetic protein-4)" is a member of the bone morphogenetic protein family, and is related to the development of the bone and cartilage. Further, BMP-4 is also known to be related to the endochondral bone, muscle development, bone mineralization, and ureteric bud development, but has never been known as a component by which stem cells differentiate into corneal limbal stem cells.

According to the embodiment according to the present invention, stem cells may differentiate into corneal limbal stem cells by culturing the stem cells in a medium including BMP-4, and 100 to 200 ng/ml of the BMP-4 may be included in the medium, but the present invention is not limited thereto.

The medium including BMP-4 may include epidermal growth factor (EGF), insulin, hydrocortisone, ethanolamine, phosphoethanolamine, bovine pituitary extract (BPF), and the like, but are not limited thereto.

For example, the medium may be prepared by adding BMP-4 to a medium in which a medium including epidermal growth factor (EGF), insulin, hydrocortisone, ethanolamine, phosphoethanolamine and bovine pituitary extract (BPF) and an Iscove's modified Dulbecco's medium (IMDM) supplemented with fetal bovine serum (FBS) are mixed in a ratio of 1:2 to 2:1.

Further, the medium may be prepared by adding BMP-4 to a medium in which a medium including epidermal growth factor (EGF), insulin, hydrocortisone, ethanolamine, phosphoethanolamine and bovine pituitary extract (BPF) and an Iscove's modified Dulbecco's medium (IMDM) supplemented with fetal bovine serum (FBS) are mixed in a ratio of 1:1.

According to the embodiment according to the present invention, stem cells may be differentiated into corneal limbal stem cells using a method including: culturing a stem cell in a medium for 2 to 5 days, preferably, for 2 to 3 days, the medium prepared by adding BMP-4 to a medium in which a medium including epidermal growth factor (EGF), insulin, hydrocortisone, ethanolamine, phosphoethanolamine and bovine pituitary extract (BPF) and an Iscove's modified Dulbecco's medium (IMDM) supplemented with fetal bovine serum (FBS) are mixed in a ratio of 1:2 to 2:1; and further culturing the cultured stem cell in a medium for 15 to 30 days, the medium in which a medium including epidermal growth factor (EGF), insulin, hydrocortisone, ethanolamine, phosphoethanolamine and bovine pituitary extract (BPF) and an Iscove's modified Dulbecco's medium (IMDM) supplemented with fetal bovine serum (FBS) are mixed in a ratio of 1:2 to 2:1.

Further, when BMP-4 is included in the medium according to the present invention, 100 to 200 ng/ml, preferably, 100 to 125 ng/ml of the BMP-4 may be included in the medium. When the concentration of the BMP-4 in the medium is out of the above-described range, stem cells may not differentiate into corneal limbal stem cells.

In the present invention, the term "corneal limbal stem cell" refers to a stem cell which is present at the corneal limbus in which the cornea epithelial stem cell is positioned, and also refers to a stem cell involved in the maintenance and reproduction of corneal tissue. Accordingly, when the corneal limbal stem cell is transplanted to the cornea of the patient whose vision is impaired or lost due to a damaged cornea, the damaged cornea may be restored, and the patient may recover his or her vision.

In this point of view, the present invention relates to a pharmaceutical composition for treating corneal damage, including a corneal limbal stem cell differentiated from a stem cell using the method according to the present invention as an active ingredient.

The corneal damage denotes the case in which vision is impaired or lost due to a lack of partial or entire limbal stem cells due to congenital or acquired physical impairments, chemical burns, pathological reasons, injury, or the like, or due to the non-renewable corneal damage, but is not limited thereto. The case in which vision impaired or lost due to pathological reasons may include Stevens-Johnson syndrome, but is not limited thereto.

When the composition according to the present invention is used as a pharmaceutical composition, various compositions may be prepared by mixing with a pharmaceutically acceptable carrier. For example, a binder, a lubricant, a disintegrating agent, an excipient, a solubilizer, a dispersing agent, a stabilizer, a suspending agent, a pigment, a flavor or the like may be mixed and used as the pharmaceutically acceptable carrier. For an injectable formulation, a buffer, a preservative, an analgesic, a solubilizer, an isotonic agent, a stabilizer or the like may be mixed and used. The injectable composition may be formulated in unit dosage ample or multi dosage form. For topical administration, the composition according to the present invention may include a base, an excipient, a lubricant, a preservative or the like. However, the present invention is not limited thereto, those skilled in the art may formulate the pharmaceutical composition for treating corneal damage in various forms, and a diversity of carriers or additives may be additionally included.

Further, the administration route of the pharmaceutical composition according to the present invention is not limited insofar as differentiated corneal limbal stem cells may reach the position of the eye at which the differentiated corneal limbal stem cells may serve to maintain and regenerate corneal tissue, and for example, may be administered to a portion of the eyes, the inside of the vitreous humour, the periphery of the eyes, a cornea, a conjunctiva, the inside of the anterior chamber, the under part of the cornea, the under part of the conjunctiva, a limbus, or the like, but the present invention is not limited thereto.

The therapeutically effective amount of the pharmaceutical composition for treating corneal damage according to the present invention denotes the dosage required for the pharmaceutical composition to exhibit the effect of maintenance and regeneration of corneal tissues. Accordingly, the dosage may be adjusted according to the conditions, the severity of the disease, age, gender, body weight, health conditions and dietary status of the patient, the time and method of administration of the composition, the route of administration of the composition and excretion rate.

According to the embodiment of the present invention, the administration of the pharmaceutical composition for treating corneal damage may denote transplantation, for example, the administration of corneal limbal stem cells may denote the transplantation of corneal limbal stem cells.

According to the embodiment of the present invention, a method of inducing differentiation of a stem cell into a corneal limbal stem cell and a pharmaceutical composition for treating corneal damage, including a differentiated corneal limbal stem cell as an active ingredient are provided, and the differentiated corneal limbal stem cell is transplanted to the cornea of patients whose vision is impaired or lost due to corneal damage to recover vision of the patients and resolve the problem of a lack of donated corneas, and thus the present invention is expected to substitute for limbal tissue transplantation from donated corneas.

BRIEF DESCRIPTION OF THE DRAWINGS

FIG. 2A shows an induced pluripotent stem cell (low magnification, 100×), FIG. 2B shows the induced pluripotent stem cell (high magnification, 200×), FIG. 2C shows a corneal limbal stem cell differentiated after culturing an induced pluripotent stem cell in a medium not including BMP-4 (high magnification, 200×), and FIG. 2D shows a corneal limbal stem cell differentiated after culturing an induced pluripotent stem cell in a medium including BMP-4 (high magnification, 200×).

FIGS. 3A, B and C respectively show the results of immunohistochemical staining by which the expression changes of markers in an induced pluripotent stem cell, a corneal limbal stem cell differentiated after culturing an induced pluripotent stem cell in a medium not including BMP-4, and a corneal limbal stem cell differentiated after culturing an induced pluripotent stem cell in a medium including BMP-4 were observed. FIG. 3D shows the result of determining the expression changes of markers depending on whether BMP-4 is included in the medium or not, using real time PCR, where a "PI" represents a corneal limbal stem cell differentiated after culturing an induced pluripotent stem cell in a medium not including BMP-4, and a "BMP4" represents a corneal limbal stem cell differentiated after culturing an induced pluripotent stem cell in a medium including BMP-4.

DETAILED DESCRIPTION

Hereinafter, the embodiments of the present invention will be described in detail. However, the following embodiments merely exemplify the present invention, and the present invention is not limited thereto.

Example 1. Inducement of Differentiation of Induced Pluripotent Stem Cell into Corneal Limbal Stem Cell 1-1. Differentiation-Inducing Medium A medium prepared by mixing Panserin 801 medium (PAN-Biotech GmbH, Germany) which is known as a medium for culturing human corneal epithelial cells and Icove's modified Dulbecco's medium (Welgene Inc., Korea of Republic) which promotes cell proliferation, and further mixing bone morphogenetic protein-4 (BMP-4) thereto was used. A specific method of preparing the medium is as follows.

1) preparing a medium in which Icove's modified Dulbecco's medium and 10%-fetal bovine serum were mixed.
2) preparing a Panserin 801 medium (epidermal growth factor (EGF)+insulin+hydrocortisone+ethanolamine+phosphoethanolamine+pituitary extract).
3) preparing a medium in which the medium prepared in step 1) and the medium prepared in step 2) are mixed in the ratio of 1:1.
4) preparing a differentiation-inducing medium by adding BMP-4 at a concentration of 100 ng/ml to the medium prepared in step 3).

1-2. Culture Method

An induced pluripotent stem cell (Human iPS: HPS0002: 253G1, Riken, Japan) was cultured in the differentiation-inducing medium prepared in step 4) of Example 1-1 for 3 days, and then was further cultured in the mixed medium prepared in step 3) of Example 1-1 for 4 weeks while the medium was replaced by a fresh one every other day. As a comparative experimental group, an induced pluripotent stem cell was cultured in the mixed medium prepared in step 3) of Example 1-1 for 4 weeks while the medium was replaced by a fresh one every other day.

Example 2. Determination of Differentiation of Induced Pluripotent Stem Cell into Corneal Limbal Stem Cell

2-1. Determination of Shape of Cell

In order to determine that an induced pluripotent stem cell differentiated into a corneal limbal stem cell through Example 1, the shape of a differentiation-induced cell was determined using a microscope.

Figure 1:
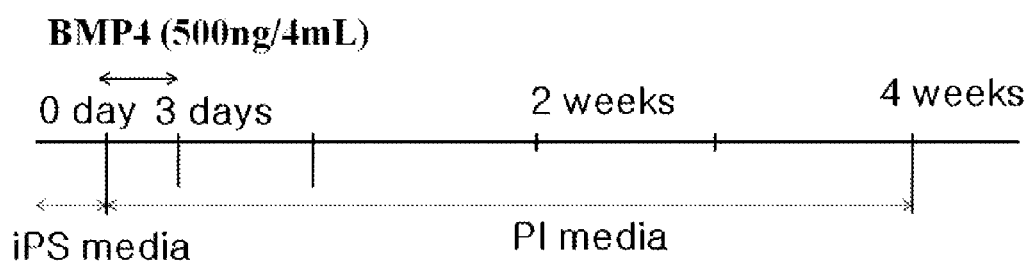
FIG. 1 shows a schematic view of a culture method for inducing differentiation of an induced pluripotent stem cell into a corneal limbal stem cell according to an embodiment of the present invention. An "iPS media" represents a medium for culturing a cell dedifferentiated into an induced pluripotent stem cell, and a "PI media" represents a medium for inducing differentiation of an induced pluripotent stem cell into a corneal limbal stem cell.
Figure 2:
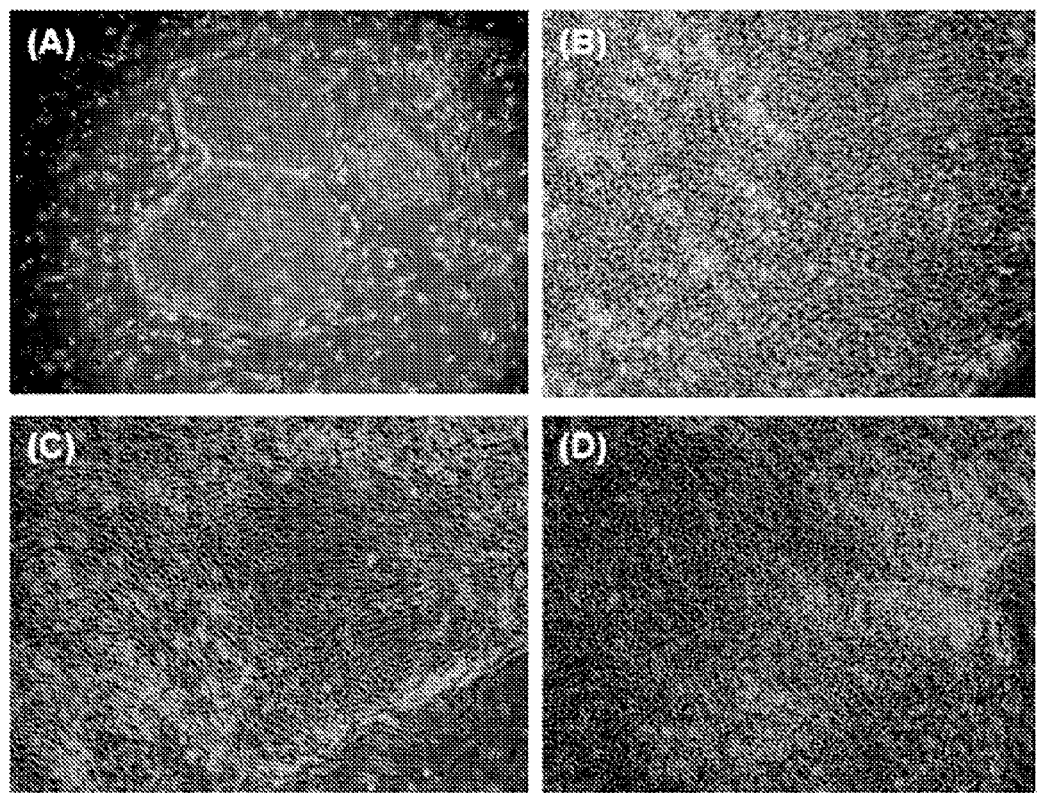
FIG. 2 shows the result of observing the shape of cells using a microscope after inducing differentiation of an induced pluripotent stem cell into a corneal limbal stem cell according to the embodiment of the present invention.

As a result, as can be seen from FIG. 2, it was determined that the density of cells which were differentiated to have a round-spindle shape like a corneal limbal stem cell was more increased when an induced pluripotent stem cell was cultured in the differentiation-inducing medium prepared in step 4) of Example 1-1 to which BMP-4 was added and then was further cultured in the medium prepared in step 3) of Example 1-1 for 4 weeks (FIG. 2D), as compared to when an induced pluripotent stem cell was cultured only in the medium prepared in step 3) of Example 1-1 for 4 weeks (FIG. 2C).

2-2. Determination of Expression Changes of Markers of Epithelial Cell and Corneal Limbal Stem Cell In order to determine that an induced pluripotent stem cell was differentiated into a corneal limbal stem cell, real time PCR and immunohistochemical staining were carried out to determine change in the expression of K3 which is a marker of epithelial cells and the expression of ABCG2 and p63 which are markers of corneal limbal stem cells. First, in order to carry out real time PCR, cells differentiated from induced pluripotent stem cells cultured for 4 weeks were isolated, and RNAs were isolated therefrom using a Trizol and RNeasy mini kit (Qiagen, USA) to be quantified using a biophotometer. A reverse transcription process was carried out using SuperScript III™ reverse transcriptase (Invitrogen) in order to analyze the expression of each mRNA using an RT-PCR method. The reverse transcription reaction was induced using a random primer from 2 μg of RNA, RNA was incubated at 25° C. for 10 minutes, and the process was further carried out at 37° C. for 120 minutes. A PCR reaction was induced by adding 12.5 μl of TaqMan Universal PCR MasterMix, 1.25 μl of gene-specific primer/probe mix (Applied Biosystems, Lincoln, Calif., USA), and 6.25 μl of PCR grade water to 100 ng of cDNA. Here, PCR started with the reaction at 95° C. for 10 minutes, and was performed with 40 cycles of the reaction at 95° C. for 15 seconds and at 60° C. for 1 minute. The expression of each mRNA was measured through an ABI 7000 real-time sequence detection system (Applied Biosystems). The expression rate of mRNA was calculated by comparison with the product differentiated from iPS cells cultured in the medium to which BMP-4 was added based on the product differentiated from iPS cells cultured in a PI media, using a comparative CT method (threshold cycle). Primer sequences used in the reaction are given below:

```
                                    (SEQ ID NO: 1)
K3-F:        GGCA GAGA TCGA GGGT GTC (SEQ ID NO: 2)
K3-R:        GTCA TCCT TCGC CTGC TGTA G (SEQ ID NO: 3)
ABCG2-F:     ACCA TTGC ATCT TGGC TGTC (SEQ ID NO: 4)
ABCG2-R:     CGAT GCCC TGCT TTAC CAAA (SEQ ID NO: 5)
p63-F:       CAA CTG CTC AAA GGC ACA AA (SEQ ID NO: 6)
p63-R:       CCT CCC AGG AAA CAA CAG AA
```

Further, in order to carry out immunohistochemical staining, cells differentiated from induced pluripotent stem cells cultured for 4 weeks were fixed with 4% paraformaldehyde for 15 minutes, were cleaned using PBS, bovine serum was applied to the cells for 30 minutes to suppress a non-specific reaction, the serum was removed, the cells were reacted with primary antibodies to K3 and ABCG2 at room temperature for 1 hour, and were washed using PBS. Subsequently, fluorescent secondary antibodies were applied to the cells for 30 minutes, were washed using PBS, and the cells were covered with cover glass using VECTASHIELD mounting medium with DAPI and were observed.

Figure 3:
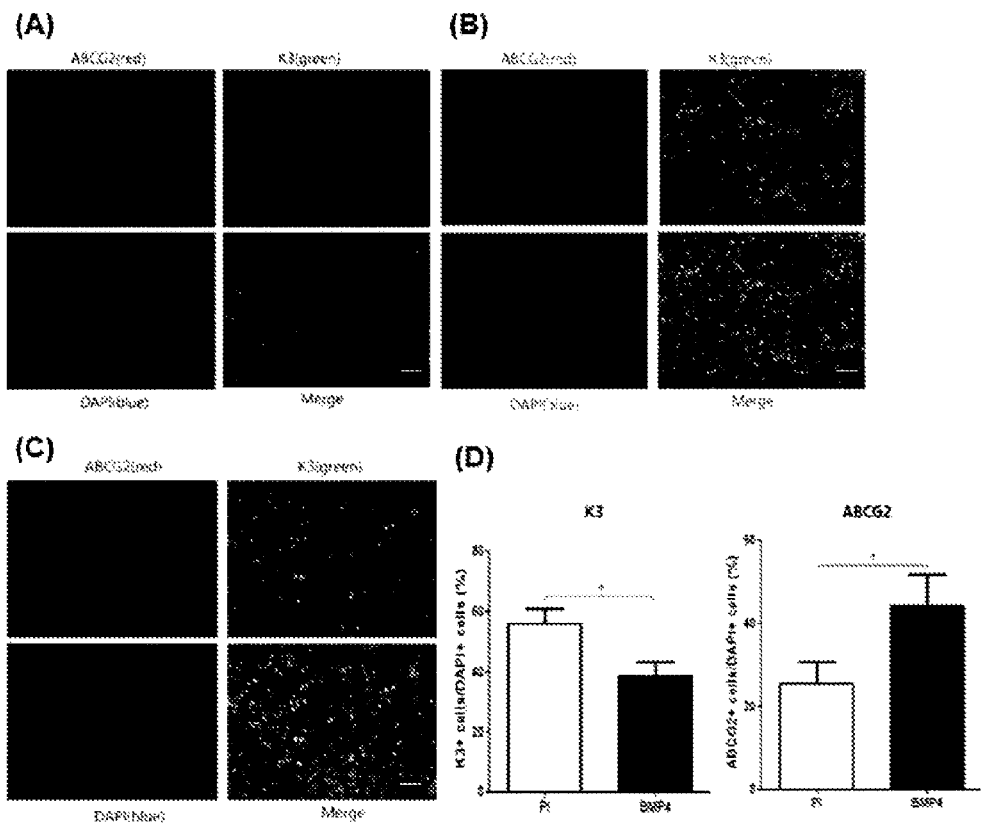
FIG. 3 shows the result of determining the expression changes of ABCG2 which is a marker of a corneal limbal stem cell and K3 which is a marker of a corneal epithelial cell, after inducing differentiation of an induced pluripotent stem cell into a corneal limbal stem cell according to the embodiment of the present invention.

As a result, as can be seen from FIG. 3, the expression of K3 which is a marker of epithelial cells was further decreased and the expression of ABCG2 which is a marker of corneal limbal stem cells was further increased when an induced pluripotent stem cell was cultured in the differentiation-inducing medium prepared in step 4) of Example 1-1 to which BMP-4 was added and then was further cultured in the medium prepared in step 3) of Example 1-1 for 4 weeks (FIG. 3C), as compared to when an induced pluripotent stem cell (FIG. 3A) was cultured only in the medium prepared in step 3) of Example 1-1 for 4 weeks (FIG. 3B).

Figure 4:
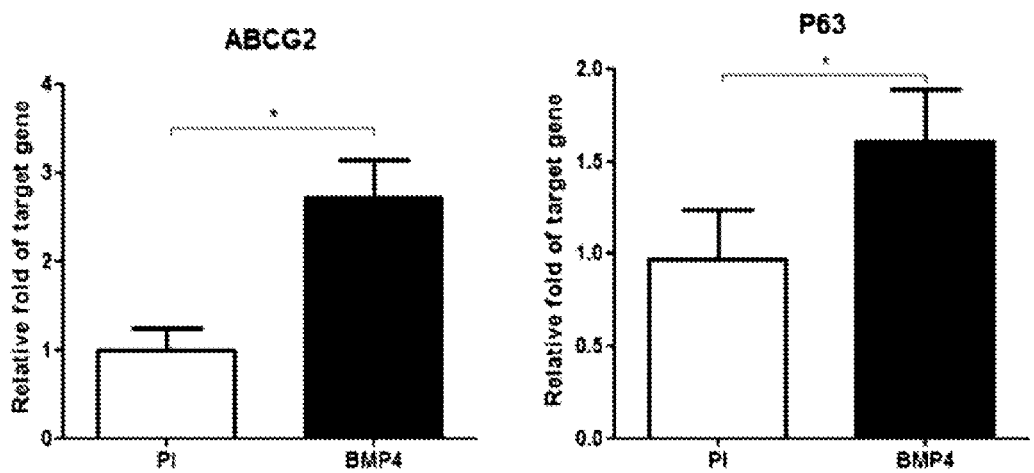
FIG. 4 shows the result of determining the expression changes of ABCG2 and p63 which are markers of a corneal limbal stem cell using real time PCR, after inducing differentiation of an induced pluripotent stem cell into a corneal limbal stem cell according to the embodiment of the present invention. A "PI" represents a corneal limbal stem cell differentiated after culturing an induced pluripotent stem cell in a medium not including BMP-4, and a "BMP4" represents a corneal limbal stem cell differentiated after culturing an induced pluripotent stem cell in a medium including BMP-4.

Further, as can be seen From FIG. 4, the expression of ABCG2 and p63 which are markers of corneal limbal stem cells were further increased when an induced pluripotent stem cell was cultured in the differentiation-inducing medium prepared in step 4) of Example 1-1 to which BMP-4 was added and then was further cultured in the medium prepared in step 3) of Example 1-1 for 4 weeks (FIG. 4, BMP4), as compared to when an induced pluripotent stem cell was cultured only in the medium prepared in step 3) of Example 1-1 for 4 weeks (FIG. 4, PI).

What is claimed is:

1. A method of inducing differentiation of a mouse or human induced pluripotent stem (iPS) cell or a mouse or human embryonic stem (ES) cell into a corneal limbal stem cell, comprising:
   (i) culturing the iPS or ES cell in a first mixed medium supplemented with bone morphogenetic protein-4 (BMP-4) for 2 to 5 days; and
   (ii) culturing the iPS or ES cell of (i) in a second mixed medium not supplemented with BMP-4 for 15 to 30 days,
   wherein the first and the second mixed mediums are a mixture of the following: a medium including epidermal growth factor (EGF), insulin, hydrocortisone, ethanolamine, phosphoethanolamine and bovine pituitary extract (BPF); and an Iscove's modified Dulbecco's medium (IMDM) supplemented with fetal bovine serum (FBS); wherein the mixture is at a ratio of 1:2 to 2:1, thereby inducing the differentiation of the iPS or ES cell of (ii) into a corneal limbal stem cell.

2. The method of claim 1, wherein 100 to 200 ng/ml of the BMP-4 is included in the first mixed medium.

3. A medium composition for inducing differentiation of a mouse or human iPS cell or a mouse or human ES cell into a corneal limbal stem cell, comprising a mixed medium supplemented with BMP-4,
   wherein the mixed medium is mixture of a medium comprising EGF, insulin, hydrocortisone, ethanolamine, phosphoethanolamine and BPF, and an IMDM supplemented with FBS at a ratio of 1:2 to 2:1.

4. The medium composition of claim 3, wherein the BMP-4 is present at a concentration of 100 to 200 ng/ml.

5. The method of claim 1, wherein the iPS or ES cell is cultured in the presence of BMP-4 for three days and cultured in the absence of BMP-4 for four weeks.

* * * * *